United States Patent
Trumbull et al.

(10) Patent No.: US 9,053,352 B2
(45) Date of Patent: Jun. 9, 2015

(54) HIGH THROUGHPUT, OPTICAL METHOD AND SYSTEM FOR DETERMINING THE EFFECT OF A TEST SUBSTANCE ON NON-CONTIGUOUS LIVING CELLS

(75) Inventors: Jonathan D. Trumbull, Chicago, IL (US); Gary A. Gintant, Libertyville, IL (US); Stanislaw Kantor, Buffalo Grove, IL (US); Jeffrey Yen Pan, Lake Forest, IL (US); Gilbert J. Diaz, Mount Prospect, IL (US); Jonathon Green, Elgin, IL (US); Zhi Su, Vernon Hills, IL (US); Jeffrey A. Olson, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 538 days.

(21) Appl. No.: 13/294,848

(22) Filed: Nov. 11, 2011

(65) Prior Publication Data

US 2012/0134570 A1    May 31, 2012

Related U.S. Application Data

(60) Provisional application No. 61/413,201, filed on Nov. 12, 2010.

(51) Int. Cl.
*G06K 9/00* (2006.01)
*C12M 1/34* (2006.01)
*G06T 7/00* (2006.01)
(Continued)

(52) U.S. Cl.
CPC ......... *G06K 9/00127* (2013.01); *C12M 1/3446* (2013.01); *G06T 7/0012* (2013.01); *B01L 3/5027* (2013.01); *G01N 15/1475* (2013.01); *G06T 7/0016* (2013.01); *G06T 2207/10016* (2013.01); *G06T 2207/30024* (2013.01)

(58) Field of Classification Search
None
See application file for complete search history.

(56) References Cited

U.S. PATENT DOCUMENTS 4,208,483 A * 6/1980 Lee ............................. 435/299.1
4,559,299 A * 12/1985 Rotman ......................... 435/29
4,839,292 A * 6/1989 Cremonese ................ 435/297.2
(Continued)

FOREIGN PATENT DOCUMENTS

DE         4411661 A1    10/1995
JP         55060855 A  *  5/1980 ............. G01N 35/02
JP       2003325163 A  * 11/2003 ............... C12M 3/00

OTHER PUBLICATIONS

International Preliminary Report on Patentability and Written Opinion for Application No. PCT/US2011/060459, mailed on May 14, 2013, 16 pages.

(Continued)

*Primary Examiner* — Wenpeng Chen
(74) *Attorney, Agent, or Firm* — Lisa V. Mueller; Michael Best & Friedrich LLP

(57) ABSTRACT

A rapid and efficient method and apparatus for detecting electrophysiologic, proarrhythmic, contractile, and other effects of substances such as compounds and drugs in native cellular cardiac preparations, the preparations representing an integrated cell-based pharmacologic response is disclosed. More specifically, a method to (1) rapidly and efficiently detect and verify the effects of chemicals, compounds and drugs on cardiac repolarization, contractility, and excitability using optically based techniques and customized simulation protocols, and (2) rapidly and efficiently screen and select compounds for electrophysiologic and proarrhythmic effects on cardiac myocytes is disclosed.

4 Claims, 8 Drawing Sheets

(51) Int. Cl.
*G01N 15/14* (2006.01)
*B01L 3/00* (2006.01)

(56) References Cited

U.S. PATENT DOCUMENTS

| | | | |
|---|---|---|---|
| 5,149,972 A * | 9/1992 | Fay et al. | 250/461.1 |
| 5,496,697 A * | 3/1996 | Parce et al. | 435/5 |
| 5,595,893 A * | 1/1997 | Pometto et al. | 435/136 |
| 5,866,430 A | 2/1999 | Grow | |
| 6,569,654 B2 * | 5/2003 | Shastri et al. | 435/173.8 |
| 6,653,124 B1 * | 11/2003 | Freeman | 435/297.1 |
| 6,690,817 B1 * | 2/2004 | Cabib et al. | 382/134 |
| 6,727,071 B1 * | 4/2004 | Dunlay et al. | 435/7.21 |
| 6,831,994 B2 * | 12/2004 | Bridgham et al. | 382/133 |
| 6,953,550 B2 * | 10/2005 | Sheppard et al. | 422/63 |
| 7,172,804 B2 * | 2/2007 | Kelso | 428/206 |
| 7,546,210 B2 * | 6/2009 | Callahan et al. | 702/19 |
| 7,817,840 B2 * | 10/2010 | Mattheakis et al. | 382/133 |
| 7,842,499 B2 * | 11/2010 | Murphy et al. | 435/288.4 |
| 7,907,769 B2 * | 3/2011 | Sammak et al. | 382/133 |
| 8,189,900 B2 * | 5/2012 | Sammak et al. | 382/133 |
| 8,673,627 B2 * | 3/2014 | Nobile et al. | 435/287.2 |
| 2002/0028480 A1 * | 3/2002 | Maher et al. | 435/40 |
| 2002/0034796 A1 * | 3/2002 | Shastri et al. | 435/173.1 |
| 2002/0085995 A1 * | 7/2002 | Sullivan et al. | 424/93.7 |
| 2002/0090122 A1 * | 7/2002 | Baer et al. | 382/133 |
| 2002/0179457 A1 * | 12/2002 | Heller | 205/775 |
| 2003/0082632 A1 * | 5/2003 | Shumate | 435/7.1 |
| 2003/0129296 A1 * | 7/2003 | Kelso | 427/2.1 |
| 2005/0035001 A1 * | 2/2005 | Yasuda et al. | 205/673 |
| 2005/0048575 A1 * | 3/2005 | Coassin et al. | 435/7.1 |
| 2005/0054028 A1 | 3/2005 | Teich et al. | |
| 2005/0074834 A1 * | 4/2005 | Chaplen et al. | 435/34 |
| 2005/0277168 A1 | 12/2005 | Wood | |
| 2005/0282208 A1 * | 12/2005 | Adams et al. | 435/6 |
| 2006/0141617 A1 * | 6/2006 | Desai et al. | 435/325 |
| 2006/0160169 A1 * | 7/2006 | Marcotte et al. | 435/34 |
| 2006/0166184 A1 * | 7/2006 | Yasuda et al. | 435/4 |
| 2006/0234332 A1 * | 10/2006 | Mattheakis et al. | 435/40.5 |
| 2006/0275745 A1 * | 12/2006 | Schwarz | 435/4 |
| 2007/0099189 A1 * | 5/2007 | Gomez-Elvira Rodriguez et al. | 435/6 |
| 2007/0202487 A1 * | 8/2007 | Fan | 435/4 |
| 2008/0131323 A1 * | 6/2008 | Kuczenski et al. | 422/82.13 |
| 2008/0279441 A1 * | 11/2008 | Matsuo et al. | 382/133 |
| 2008/0299169 A1 * | 12/2008 | Hoffman-Kim et al. | 424/423 |
| 2009/0042280 A1 * | 2/2009 | Yang et al. | 435/287.2 |
| 2009/0142790 A1 * | 6/2009 | Fang et al. | 435/29 |
| 2009/0202614 A1 * | 8/2009 | Kaplan et al. | 424/443 |
| 2009/0203536 A1 * | 8/2009 | Vermette et al. | 506/9 |
| 2009/0250130 A1 * | 10/2009 | Studer et al. | 137/833 |
| 2009/0258383 A1 * | 10/2009 | Kovac et al. | 435/29 |
| 2009/0290151 A1 * | 11/2009 | Agrawal et al. | 356/318 |
| 2009/0325215 A1 * | 12/2009 | Okano et al. | 435/29 |
| 2010/0002929 A1 * | 1/2010 | Sammak et al. | 382/133 |
| 2010/0221836 A1 * | 9/2010 | Rickus et al. | 435/404 |
| 2010/0291584 A1 * | 11/2010 | Tseng et al. | 435/6 |
| 2010/0300895 A1 * | 12/2010 | Nobile et al. | 205/775 |
| 2011/0201099 A1 * | 8/2011 | Anderson et al. | 435/287.2 |
| 2011/0206262 A1 * | 8/2011 | Sammak et al. | 382/133 |
| 2011/0216953 A1 * | 9/2011 | Callahan et al. | 382/128 |
| 2011/0286888 A1 * | 11/2011 | Barlag | 422/82.01 |
| 2012/0220022 A1 * | 8/2012 | Ehrlich et al. | 435/286.2 |
| 2012/0328488 A1 * | 12/2012 | Puntambekar et al. | 422/503 |
| 2012/0329675 A1 * | 12/2012 | Olson et al. | 506/10 |

OTHER PUBLICATIONS

Chariot D., et al., "Automated Calcium Measurements in Live Cardiomyocytes," IEEE, 2008, pp. 316-319.

Cheng W., et al., "Metabolic Monitoring of the Electrically Stimulated Single Heart Cell within a Microfluidic Platform," Lab Chip, 2006, vol. 6 (11), pp. 1424-1431.

Gervais-Pingot V., et al., "In Vitro Quantification by Image Analysis of Inotropic and Chronotropic Effects of Drugs on Cultures of Cardiac Myocytes," Cell Biology and Toxicology, 1994, vol. 10 (5-6), pp. 297-300.

Hansen A., et al., "Development of a Drug Screening Platform Based on Engineered Heart Tissue," Circulation Research, 2010, vol. 107 (1), pp. 35-44.

Harary I., et al., "A Video-Computer for the Chronotropic and Inotropic Measurements of the Beating of Cultured Heart Cells," Cytometry, 1983, vol. 3 (5), pp. 367-375.

Hardy M.E., et al., Can Optical Recordings of Membrane Potential be Used to Screen for Drug-Induced Action Potential Prolongation in Single Cardiac Myocytes?, Journal of Pharmacological and Toxicological Methods, 2006, vol. 54 (2), pp. 173-182.

He J.Q., et al., "Human Embryonic Stem Cells Develop into Multiple Types of Cardiac Myocytes: Action Potential Characterization," Circulation Research, 2003, vol. 93 (1), pp. 32-39.

International Search Report for Application No. PCT/US2011/060459, mailed on Jul. 12, 2012, 8 pages.

Klauke N., et al., "Stimulation of Isolated Ventricular Myocytes Within an Open Architecture Microarray," IEEE Transactions on Biomedical Engineering, 2005, vol. 52 (3), pp. 531-538.

Stummann T.C., et al., "Digital Movie Analysis for Quantification of Beating Frequencies, Chronotropic Effects, and Beating Areas in Cardiomyocyte Cultures," Assay and Drug Development Technologies, 2008, vol. 6 (3), pp. 375-385.

Vasudevan A., et al., "Lophtor: A Convenient Flow-Based Photochemical Reactor," Tetrahedron Letters, 2010, vol. 51, pp. 4007-4009.

Yokoo N., et al., "The Effects of Cardioactive Drugs on Cardiomyocytes Derived from Human Induced Pluripotent Stem Cells," Biochemical and Biophysical Research Communications, 2009, vol. 387 (3), pp. 482-488.

European Search Report for Application No. EP2838053, mailed on Mar. 4, 2015, 10 pages.

* cited by examiner

Plasma polymerization of allylamine can functionalize a surface with primary amines

HIGH THROUGHPUT, OPTICAL METHOD AND SYSTEM FOR DETERMINING THE EFFECT OF A TEST SUBSTANCE ON NON-CONTIGUOUS LIVING CELLS

RELATED APPLICATION INFORMATION

This application claims priority to U.S. Provisional Patent Application Ser. No. 61/413,201, filed Nov. 12, 2010, which is incorporated by reference in its entirety.

FIELD OF THE INVENTION

The invention relates generally to methods for determining the effect of a substance, and more particularly, to a method and apparatus for rapidly detecting and measuring electro physiologic, proarrhythmic, inotropic and other effects of substances in vitro, on living cells, based on such detection protocols as contractile responses, optical detection schemes and customized, programmed electrical stimulation.

BACKGROUND OF THE INVENTION

Current methods for evaluating the various effects of drugs on cardiac or other biologic tissues in vitro routinely use time-consuming and technically-complex intracellular recording techniques. Further, in most cases, these evaluations are generally applied to syncytial preparations or to isolated cells one at a time.

Typically, intracellular recordings obtained in the absence and/or the presence of various substances are compared for evidence of the effects of those various substances on a muscle fiber's cardiac action potential. Among other aspects, a substance may affect a muscle fiber's cardiac action potential by delaying cardiac repolarization (manifested as prolongation of the action potential duration or APD) or accelerate cardiac repolarization (manifested as the shortening of the APD).

Unfortunately, several inadequacies exist: The current methods for obtaining these intracellular recordings are difficult to maintain; the experiments used to obtain the intracellular recordings are slow, primarily as a result of long drug equilibration times, especially for cardiac muscles; and the intracellular recordings require tissue harvests from multiple specimens to ensure adequate sample sizes. In addition, this approach does not evaluate on the potential effect of a substance to affect contractility (an inherent property of many excitable tissues) or changes in excitability (another inherent property of many excitable tissues).

Delayed cardiac repolarization is considered a surrogate marker for cardiac proarrythmia (and in particular, Torsades-de-Pointes). It has been repeatedly demonstrated that the effects of substances that delay cardiac repolarization are exaggerated during slower stimulation, an effect termed "reverse use-dependence." Unfortunately, the effects of substances during accelerated (or irregular) pacing are typically not considered. This may be crucial in the evaluation of proarrhythmic risk associated with the rare, drug-induced polymorphic ventricular tachycardia known as Torsades-de-Pointes, as the initiating rhythm typically involves an irregular stimulation pattern or premature beats.

Integrated cellular responses, such as those provided from isolated myocytes, are preferred to evaluate the electrophysiology effects of substances on a body, as it is essentially unknown which cardiac ion channels or contractile proteins may be affected by chemicals and/or compounds under evaluation for safety or efficacy.

The ability of a living cell to respond mechanically (i.e., to either expand or contract) to a stimulus, particularly electrical stimulation, is dependent, inter alia, upon the recovery of the cell from prior electrical stimulation. In other words, expansion or contraction of a cell due to electrical stimulation is partially dependent on the quickness of a cell's "return to normal" bias, or repolarization, from a previous electrical stimulation. In the case of cardiac cells, this responsive ability is referred to as refractoriness, which is closely linked to the "cardiac action potential."

A cell's cardiac action potential can be affected by many factors. For instance, the introduction/exposure of substances to a cell has been shown to have an effect on cardiac action potential. Some substances, like drugs and/or other chemicals, that delay repolarization and prolong the duration of the cardiac action potential, are said to prolong refractoriness. As an example, substances enhancing either the inward ionic (e.g., sodium or calcium) current can elicit increases in the cardiac action potential. In doing so, these substances limit the ability of a cell to respond to very rapid or premature stimulation. Through the use of such substances, refractoriness may be prolonged due to either (1) the reduction of outward repolarizing currents, or (2) the transient reduction and/or delaying of the recovery of channels conducting excitatory inward currents.

Similarly, substances that accelerate repolarization and shorten the cardiac action potential duration are said to shorten refractoriness. Changes in refractoriness have been linked to proarrhythmia. For example, delayed repolarization has been linked to ventricular proarrhythmia (including Torsades-de-Pointes), while shortened atrial repolarization (and refractoriness) has been linked to atrial proarrhthmia (such as atrial flutter and fibrillation) and ventricular fibrillation.

While changes in refractoriness can result from the effects on ionic currents, understanding a substance's effects on any individual ionic currents does not adequately predict effects on refractoriness, as multiple ionic currents can act in an integrated fashion to define refractoriness, and substances may affect multiple ionic currents in an undetermined manner at different concentrations. Thus, changes in refractoriness are typically evaluated in an intact, integrated cellular system (e.g., a muscle fiber). However, the direct electrophysiologic measures of changes (using microelectrode or patch electrode-based recording techniques) and the measurement of changes in refractoriness of integrated cellular systems are tedious, technically complex, and not amenable to higher throughput.

Thus, it is desirable to provide an improved method for detecting the effect of a substance on a body, which overcomes the disadvantages in the currently-used methodologies.

The invention provides for the evaluation of the effects, particularly electrophysiologic effects, of drugs on cells, particularly cardiac myocytes, without using the technically-demanding intracellular recording techniques of known methods, while requiring less specimen usage in a simpler manner and requiring minimal technical expertise. The invention also provides for the simultaneous assessment of changes in mechanical effects (particularly cardiac contractility) of test substances on cells while electrophysiologic parameters (changes in repolarization and excitability) are studied.

Further, the invention uses non-invasive, optical methods to determine responses, and the cells are evaluated under physiologic conditions. The detection schemes of the present invention are less demanding technically. Additionally, the detection schemes of the present invention are faster and more efficient than known approaches. Existing edge detection methods cannot easily be scaled to support many measurements from multiple cells in parallel. Edge detection is also problematic when edges are not well defined because of low image contrast, debris, or when an experimental flow cell chamber contains closely packed cells which may overlap partially. Finally, this approach is applicable to a variety of cell types (e.g., atrial and ventricular cardiac myocytes) and can be used for cells derived from any contractile tissue where a mechanical response is triggered or dependent on the recovery of electrical excitability.

SUMMARY OF THE INVENTION

The invention provides a rapid, high throughput, non-invasive, and efficient method for measuring the effects of substances such as compounds and drugs on excitable cells. The inventive method includes a method for measuring a response of a plurality of cells to a test substance by:

(1) providing a digital video recording of a plurality of cells prior to exposure to a test substance and a digital video recording of the plurality of cells after exposure to a test substance, each of the video recordings comprising a plurality of video still frames, each of the video still frames comprising a plurality of pixels, (2) selecting one or more cellular regions from each video still frame from the video recording of the plurality of cells prior to exposure to a test substance, (3) selecting a reference frame from among the video still frames of the video recording of a plurality of cells prior to exposure to a test substance and from among the video still frames of the video recording of the plurality of cells after exposure to a test substance, (4) quantitating pixel changes within each cellular region in each video still frame from the video recording of the plurality of cells prior to exposure to a test substance by comparing the one or more cellular regions of the video still frames of the video recording of a plurality of cells prior to exposure to a test substance to the one or more cellular regions of the reference frame of the video recording of a plurality of cells prior to exposure to a test substance, (5) calculating a response-time curve for each cellular region based on the quantitated pixel change versus time, (6) defining one or more regions of interest within each cellular region, (7) applying the one or more regions of interest to the video recording of the plurality of cells after exposure to a test substance and to the reference frame of the video recording of a plurality of cells after exposure to a test substance, (8) quantitating pixel changes within each region of interest in each video still frame from the video recording of the plurality of cells after exposure to a test substance by comparing the one or more regions of interest of the video still frames of the video recording of a plurality of cells after exposure to a test substance to the one or more regions of interest of the reference frame of the video recording of a plurality of cells after exposure to a test substance, and (9) calculating a response-time curve for each region of interest based on the quantitated pixel change versus time.

The inventive method also includes a method for an experimental protocol for obtaining a video recording of the plurality of cells prior to exposure to the test substance and a video recording of the plurality of cells after exposure to the test substance by (1) exposing a plurality of cells to a stimulus, (2) simultaneously video recording the plurality of cells to obtain a video recording of the plurality of cells prior to exposure to a test substance, (3) exposing the plurality of cells to a test substance, (4) exposing the plurality of cells to the stimulus, and (5) simultaneously video recording the plurality of cells to obtain a video recording of the plurality of cells after exposure to a test substance.

The inventive method further includes a method for an experimental protocol for obtaining a video recording of a plurality of cells prior to exposure to the test substance and a video recording of the plurality of cells after exposure to the test substance by (1) video recording the plurality of cells prior to exposure to a test substance, (2) exposing the plurality of cells to a test substance, and (3) video recording the cells after exposure to the test substance. In a preferred embodiment, this methodology is applied where the cells are spontaneously contractile.

In certain embodiments, the inventive method provides for (1) rapidly and efficiently detecting, measuring, and/or verifying the effects of chemicals, compounds, and/or drugs on cardiac repolarization, contractility, and excitability using both optically-based techniques and customized simulation protocols, and (2) rapidly and efficiently screening and selecting compounds for electrophysiologic, and/or proarrhythmic effects (as well as effects on contractility and excitability) on living cells, especially cardiac myocytes. In preferred embodiments, the cells derive from native cardiac preparations, the preparations representing an integrated cell-based pharmacologic response.

In another aspect of the invention, an apparatus is provided to present living cells for digital imaging during measurement for response of the cells to a test substance. An apparatus in accordance with the invention serves to store and nourish the living cells until the time they are tested, to transport the living cells from one section of the apparatus to another, and to present the living cells to the digital recording apparatus while exposing the cells to a test substance, for example a drug, and optionally to an electrical stimulation protocol. An apparatus in accordance with the invention includes:

a fluid channel having a fluid inlet port at an inlet end and a fluid exit at an outlet end;

a fluid pumping device connected to the inlet port of the fluid channel;

a strip of optically transparent or semi-transparent film running through the fluid channel; the film capable of adhering to living cells;

at least one flowcell positioned over the film, the flowcell comprising a cavity having an optically transparent upper surface and side walls capable of forming a seal with the film to form an enclosed environment; and a vertical actuator connected to the at least one flowcell capable of elevating the at least one flowcell above the film or lowering the at least one flowcell on to the film.

Additional features, advantages and embodiments of the invention may be set forth or apparent from consideration of the following detailed description, drawings and claims. Moreover, both the foregoing Summary Of The Invention, and the following Detailed Description Of The Embodiments, are exemplary and intended to provide further explanation without limiting the scope of the invention, as claimed.

BRIEF DESCRIPTION OF THE DRAWINGS

The accompanying drawings, which are included to provide a further understanding of the invention and are incorporated in and constitute a part of this disclosure, illustrate preferred embodiments of the invention and, together with the Detailed Description, serve to explain the principles of the invention. In the drawings.

DETAILED DESCRIPTION OF THE EMBODIMENTS

Figure 1:
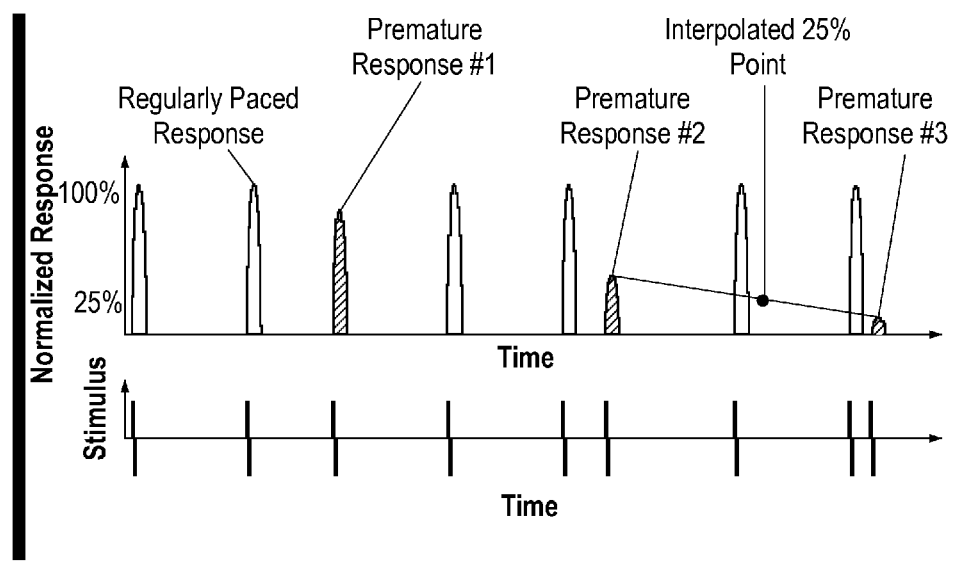
FIG. 1 illustrates an example of a response-time curve calculated in accordance with the invention and in accordance with a pre-programmed pulse protocol, shown below the response-time curve, in accordance with the invention. The pre-programmed pulse protocol depicted in FIG. 1 exhibits regularly spaced stimuli interrupted in a regular manner with premature stimuli positioned progressively closer to the regularly spaced stimuli during the course of the pulse protocol.

The present invention provides a rapid, non-invasive, and efficient method for determining the effect of a test substance (e.g., compounds or drugs) on excitable living cells. The inventive method includes a method for measuring a response of a plurality of cells to a test substance by:

(1) providing a digital video recording of a plurality of cells prior to exposure to a test substance and a digital video recording of the plurality of cells after exposure to a test substance, each of the video recordings comprising a plurality of video still frames, each of the video still frames comprising a plurality of pixels, (2) selecting one or more cellular regions from each video still frame from the video recording of the plurality of cells prior to exposure to a test substance, (3) selecting a reference frame from among the video still frames of the video recording of a plurality of cells prior to exposure to a test substance and from among the video still frames of the video recording of the plurality of cells after exposure to a test substance, (4) quantitating pixel changes within each cellular region in each video still frame from the video recording of the plurality of cells prior to exposure to a test substance by comparing the one or more cellular regions of the video still frames of the video recording of a plurality of cells prior to exposure to a test substance to the one or more cellular regions of the reference frame of the video recording of a plurality of cells prior to exposure to a test substance, (5) calculating a response-time curve for each cellular region based on the quantitated pixel change versus time, (6) defining one or more regions of interest within each cellular region, (7) applying the one or more regions of interest to the video recording of the plurality of cells after exposure to a test substance and to the reference frame of the video recording of a plurality of cells after exposure to a test substance, (8) quantitating pixel changes within each region of interest in each video still frame from the video recording of the plurality of cells after exposure to a test substance by comparing the one or more regions of interest of the video still frames of the video recording of a plurality of cells after exposure to a test substance to the one or more regions of interest of the reference frame of the video recording of a plurality of cells after exposure to a test substance, and (9) calculating a response-time curve for each region of interest based on the quantitated pixel change versus time.

In embodiments where a stimulus is applied to the plurality of cells, the stimulus may comprise a pre-programmed pacing protocol. For example, the plurality of cells may be electrically stimulated using a pre-programmed pacing protocol of consecutive, regularly paced pulse trains (each separated by a pause) wherein each train optionally increases or decreases frequency or amplitude with respect to the previous pulse train. The pre-programmed pacing protocol may also include one or more premature pulses. For example, a pre-programmed pulse protocol may exhibit regularly spaced stimuli interrupted in a regular manner with premature stimuli positioned progressively closer to the regularly spaced stimuli during the course of the pulse protocol to define refractoriness. The pre-programmed pacing protocol may also include incrementally increasing or decreasing pulse amplitudes. For example, a pre-programmed pulse protocol may exhibit stimuli with progressively decreasing amplitude or intensity during the course of the pulse protocol to define excitability.

In other embodiments of the invention, the plurality of cells are electrically excitable and respond with a change in shape, morphology, or internal rearrangement (including, but not limited to, contraction). Isolated cells, single or multiple cell clusters or islands, cell sheets or layers, or tissues may also be used. Alternatively, a plurality of cells responding to chemical or mechanical stimuli with a change in shape, morphology, or internal rearrangement may also be used. Alternatively the plurality of cells may be spontaneously active (e.g. some types of stem cells) and no stimulus may be necessary.

The inventive method included an analysis of digital video recordings of a plurality of cells taken at least two periods of time: a video recording of the plurality of cells prior to exposure to the test substance and a video recording of the plurality of cells after exposure to the test substance. In embodiments where a stimulus is applied to the plurality of cells, the video recordings are obtained by (1) exposing a plurality of cells to a stimulus, (2) simultaneously video recording the plurality of cells to obtain a video recording of the plurality of cells prior to exposure to a test substance, (3) exposing the plurality of cells to a test substance, (4) exposing the plurality of cells to the stimulus, and (5) simultaneously video recording the plurality of cells to obtain a video recording of the plurality of cells after exposure to a test substance.

Digital video recordings of the plurality of cells may also be taken while the plurality of cells is exposed to differing concentrations of a test substance.

The inventive method further includes a method for an experimental protocol for obtaining a video recording of a plurality of cells prior to exposure to the test substance and a video recording of the plurality of cells after exposure to the test substance by (1) video recording the plurality of cells prior to exposure to a test substance, (2) exposing the plurality of cells to a test substance, and (3) video recording the cells after exposure to the test substance. In a preferred embodiment, this methodology is applied where the cells are spontaneously contractile.

In certain embodiments of the invention, changes in refractoriness of a cell (e.g., a myocyte) are determined based on stimulus-derived contractile responses or an intracellular calcium transient responsible for initiating the contraction. In particular, drug effects on repolarization may be evaluated based on the ability of a plurality of cells, particularly myocytes, to contract during a programmable pacing protocol wherein the stimulation rate progressively increases or regular stimulation is interrupted with a premature stimulus. In particular, drug effects on excitability may be evaluated based on the ability of a plurality of cells, particularly myocytes, to contract during a programmable pacing protocol wherein the stimulus strength is progressively increased or decreased. These contractile effects are characterized based on the amplitude and pattern of responses, which includes the stimulation rate at which the cells fail to respond to a single stimulus, and then multiple stimuli. In other embodiments, voltage-sensitive or ion-sensitive (e.g., calcium or sodium sensitive) dyes can be employed to directly measure the electrophysiologic effects of a test substance on a cell. In such embodiments, the ability of cells to respond can be detected from changes in, for example, intracellular calcium transients as fluctuations in the emission intensity from intracellular calcium-dependent fluorescent dyes, fluctuations in the signal from voltage-sensitive dyes, or variations in microscopic image parameters such as focus or light scatter.

Figure 4:
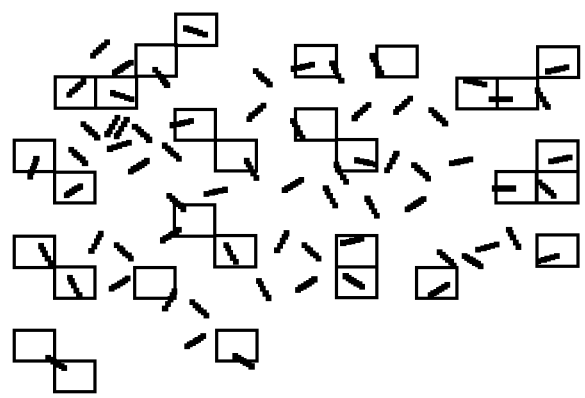
FIG. 4 illustrates the operation of optionally applying predetermined elimination criteria to the response-time curves of the cellular regions and eliminating those cellular regions corresponding with response-time curves that do not meet the predetermined elimination criteria. Depicted is a video still frame that has been segmented into cellular regions (dotted lines); solid boxes denote cellular regions that have met the predetermined exclusion criteria to become regions of interest.
Figure 5:
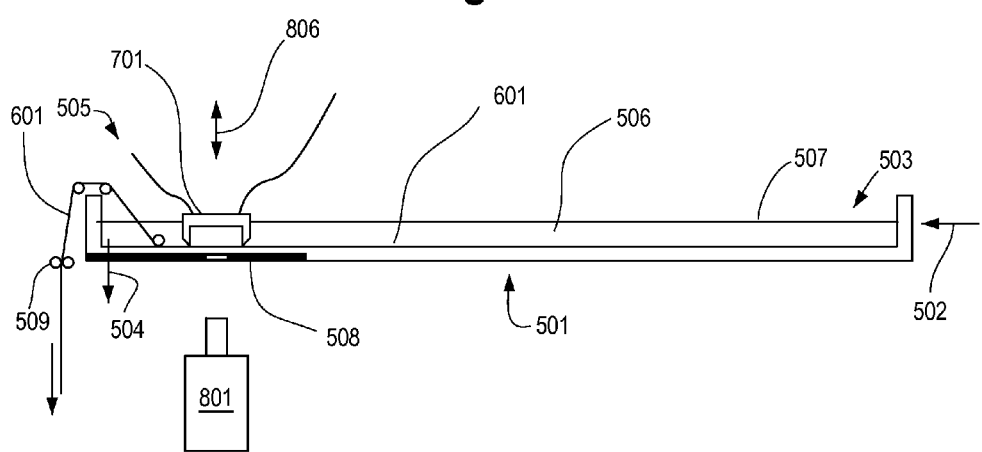
FIG. 5 is a schematic diagram illustrating an apparatus for one preferred embodiment of the invention.
Figure 6:
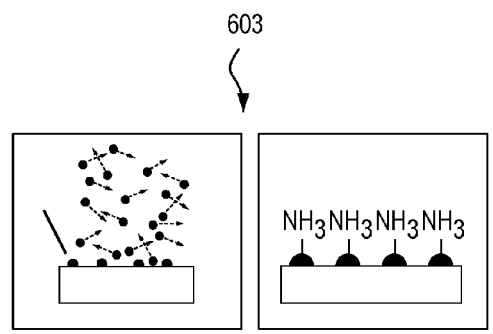
FIG. 6 is an illustration of a strip of optically transparent or semi-transparent, flexible, polymer film which can be used to transport living cells from one section to another within the apparatus of the invention
Figure 6:
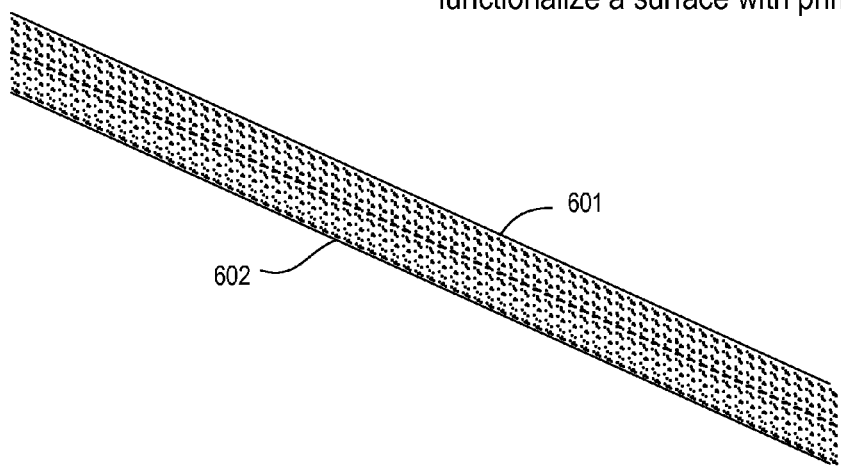
Figure 7:
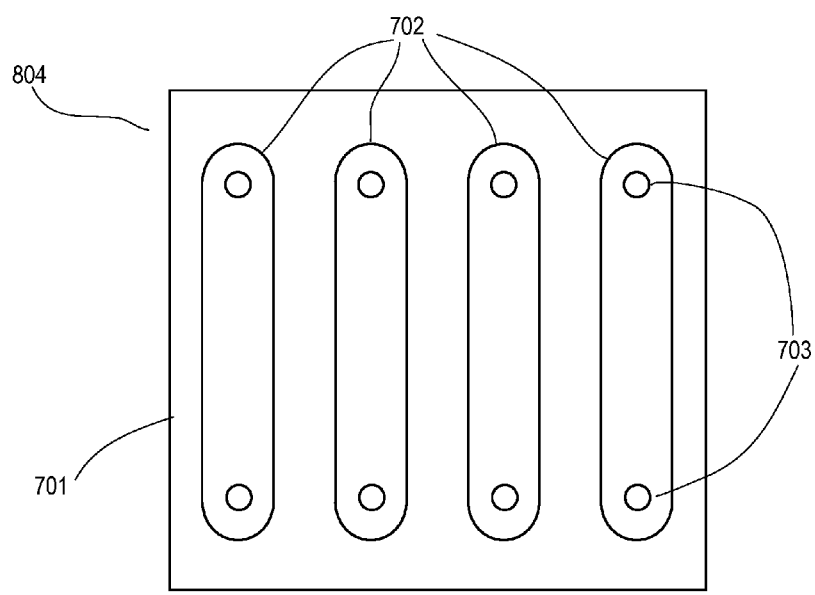
FIG. 7 is a plan view of a cluster of one or more flowcells which can be used to present the living cells to the digital recording device while exposing the living cells to a test substance and optionally administer an electrical stimulation protocol to the living cells.
Figure 8:
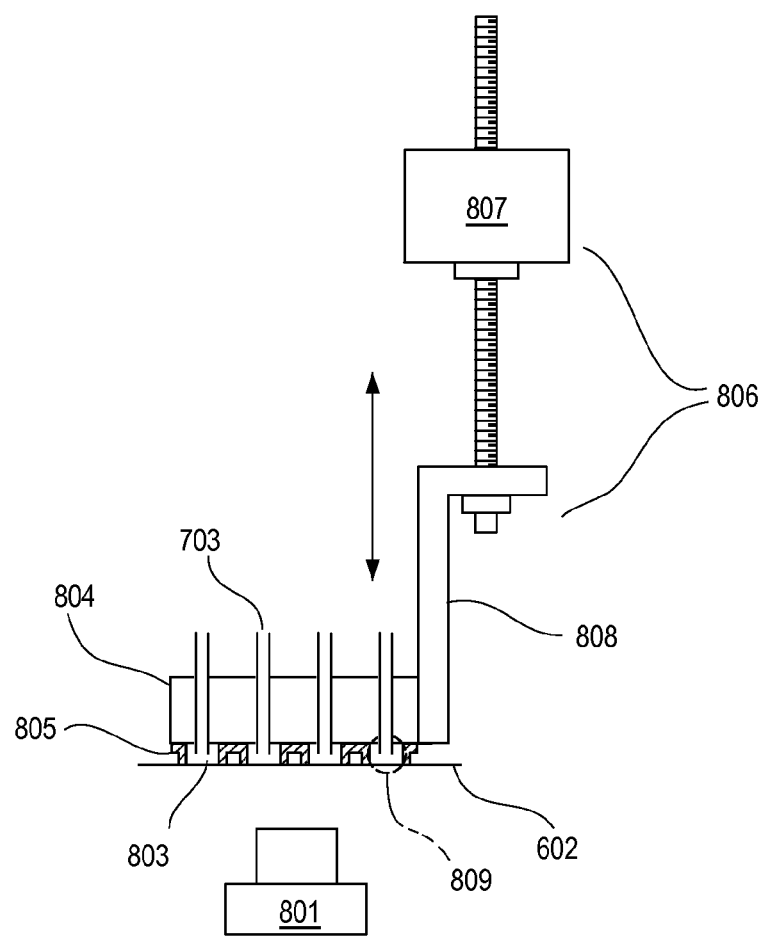
FIG. 8 is a front sectional view depicting the cluster of one or more flowcells, clamping mechanism, and a digital recording device.

In accordance with the invention, one or more cellular regions are selected from each video recording. The one or more cellular regions are selected by applying predetermined cellular region selection criteria. For example, each cellular region may correspond with each cell imaged in the video still frame to exclude the portions of each video still frame that do not image a cell. Alternately, each video still frame of the video recording may be segmented regardless of the presence, partial presence, or absence of a cell in each segment to select the cellular regions (e.g., a grid). In any embodiment, the cellular regions may be designated in an automated fashion, in which the cellular regions are derived from preprogrammed segmentation protocols, which may designate cellular regions according to predetermined criteria designed to select the portions of the video still frame corresponding with each cell imaged or by selecting regions of the video still frame as exemplified in FIG. 4. Alternately, the cellular regions may be designated by manual inspection of the video recording and segmentation or selection of the portions corresponding with each cell imaged in the video recording. Portions located outside the cellular regions may optionally be excluded from further analysis. In an embodiment of the invention, the cellular region may comprise the entirety of the video still frame.

In accordance with the invention, a video still frame from the video recording of the plurality of cells prior to exposure to the test substance is selected as a reference frame. Preferably, the reference frame is selected to coincide with a period of time in which the plurality of cells is in a state of rest. Where the plurality of cells prior to exposure to the test substance have been subjected to a stimulus, a reference frame may be chosen to coincide with a time point at which the cells are not responding to a pulse stimulus. For example, a reference frame may be chosen by determining the most likely temporal location of the cellular region's resting state, for example, by selecting the still video frame that is similar to the largest number of still video frames based on summing pixel count changes for each video frame or a subset of video frames for all possible reference locations or a subset of reference locations. Alternately, a reference frame may be chosen by determining the most likely temporal location of the cellular region's resting state by calculating a pixel intensity for each video frame, and selecting as a reference frame the video frame having the lowest or highest calculated pixel intensity depending on the whether the cellular material is darker or lighter than the surrounding space; this reference frame selection procedure is particularly preferable where the plurality of cells is spontaneously active. In another alternative, the reference frame is selected by calculating a trimmed mean of all the video still frames of the video recording of the plurality of cells prior to exposure to a test substance to form an average frame, which is selected as the reference frame of the video recording of the plurality of cells prior to exposure to a test substance.

In accordance with the invention pixel changes are quantitated within each cellular region in each video frame from the video recording of the plurality of cells prior to exposure to a test substance by comparing the one or more cellular regions of the video still frames of the video recording of a plurality of cells prior to exposure to a test substance to the one or more cellular region of the reference frame of the video recording of a plurality of cells prior to exposure to a test substance. For example, pixel changes may be quantitated by comparing each pixel from the one or more cellular regions with a corresponding pixel from the reference frame of the video recording of the plurality of cells with a corresponding pixel from the reference frame of the video recording of the plurality of cells and counting pixels that change by a preselected value. Alternately, pixel changes may be quantitated by calculating an aggregate pixel intensity of the one or more cellular regions derived from the mean, median, mode, trimmed mean or similar averaging methodology of the intensities of pixels and comparing the aggregate pixel intensity of the one or more cellular regions to the aggregate pixel intensity of the one or more cellular regions derived by performing the same averaging methodology on the one or more cellular regions of the reference frame.

A response-time curve comprising one or more peaks is calculated for each cellular region based on the amount of pixel change versus time. An example of a response-time curve calculated in accordance with the inventive method is shown in FIG. 1. Values such as contraction duration (represented as, e.g., 10-90% of total twitch); peak contraction (a measure of inotropic status); peak velocity of shortening $((+dL/dT)_{max})$, peak velocity of relaxation $(-dL/dT)$, time from initial to peak shortening $(T_{peak})$, and time from peak shortening to relaxation $(T_{peak}\text{-}90$, a measure of lusitropic status), may be calculated by analysis of the response-time curve. Aggregate values such as refractory period, loss of response to premature stimulation, noise (e.g., peak-to-height baseline noise), average peak height, and average peak width may also be calculated by analysis of the response-time curve.

One or more regions of interest are defined within each cellular region. Each cellular region may simply be defined as a region of interest, i.e., the cellular regions and regions of interest may coincide with each other. In a preferred embodiment, predetermined exclusion criteria are applied to the response-time curve; those cellular regions that do not meet the predetermined exclusion criteria are eliminated from further analysis. Categories of predetermined exclusion criteria include, for example, the values calculated from analysis of the response-time curve. For example, a cellular region may be excluded by having a response-time curve exhibiting a contraction duration outside a predetermined range of values. As a result of the application of the predetermined exclusion criteria, cellular regions containing dead, nonresponsive, or under-responsive cells may thus be excluded from further analysis and the one or more regions of interest are defined as those cellular regions having response-time curves that meet the predetermined exclusion criteria. Thus, in this preferred embodiment, regions of interest are defined to correspond with the cellular regions having cells that exhibit desirable contractile behavior.

In accordance with the invention, the regions of interest are subjected to further analysis by being applied to the video recording of the plurality of cells after exposure to a test substance. A video still frame from the video recording of the plurality of cells after exposure to the test substance is selected as a reference frame. Preferably, the reference frame selected to coincide with a period of time in which the plurality of cells is in a state of rest. Where the plurality of cells after exposure to the test substance have been subjected to a stimulus, a reference frame may be chosen to coincide with a time point at which the cells are not responding to a pulse stimulus. For example, a reference frame may be chosen by determining the most likely temporal location of the region of interest's resting state, for example, by selecting the still video frame that is similar to the largest number of still video frames based on summing pixel count changes for each video frame or a subset of video frames for all possible reference locations or a subset of reference locations. Alternately, a reference frame may be chosen by determining the most likely temporal location of the region of interest's resting state by calculating a pixel intensity for each video frame, and selecting as a reference frame the video frame having the lowest or highest calculated pixel intensity depending on the whether the cellular material is darker or lighter than the surrounding space; this reference frame selection procedure is particularly preferable where the plurality of cells is spontaneously active. In another alternative, the reference frame is selected by calculating a trimmed mean of all the video still frames of the video recording of the plurality of cells after exposure to a test substance to form an average frame, which is selected as the reference frame of the video recording of the plurality of cells after exposure to a test substance.

In accordance with the invention pixel changes are quantitated within each region of interest in each video frame from the video recording of the plurality of cells after exposure to a test substance by comparing the one or more regions of interest of the video still frames of the video recording of a plurality of cells after exposure to a test substance to the one or more regions of interest of the reference frame of the video recording of a plurality of cells after exposure to a test substance. For example, pixel changes may be quantitated by comparing each pixel from the one or more regions of interest with a corresponding pixel from the reference frame of the video recording of the plurality of cells with a corresponding pixel from the reference frame of the video recording of the plurality of cells and counting pixels that change by a preselected value. Alternately, pixel changes may be quantitated by calculating an aggregate pixel intensity of the one or more regions of interest derived from the mean, median, mode, trimmed mean or similar averaging methodology of the intensities of pixels and comparing the aggregate pixel intensity of the one or more regions of interest to the aggregate pixel intensity of the one or more regions of interest derived by performing the same averaging methodology on the one or more regions of interest of the reference frame.

Optionally, in an embodiment of the invention, sub-regions within regions of interest that do not meet predetermined sub-region elimination criteria are eliminated from further consideration. For example, sub-region elimination criteria may be based on an undesirable change in average intensity.

Optionally, to subtract slowly varying differences in pixel quantitation, a baseline correction algorithm may be applied to the one or more regions of interest.

A response-time curve comprising one or more peaks is calculated for each region of interest based on the amount of pixel change versus time. An example of a response-time curve calculated in accordance with the inventive method is shown in FIG. 1. Values such as contraction duration (represented as, e.g., 10-90% of total twitch); peak contraction (a measure of inotropic status); peak velocity of shortening ($(+dL/dT)_{max}$), peak velocity of relaxation ($-dL/dT$), time from initial to peak shortening ($T_{peak}$), and time from peak shortening to relaxation ($T_{peak}$-90, a measure of lusitropic status), may be calculated by analysis of the response-time curve. Aggregate values such as refractory period, loss of response to premature stimulation, noise (e.g., peak-to-height baseline noise), average peak height, and average peak width may also be calculated by analysis of the response-time curve.

In accordance with the invention, the response-time curves may then be compared for the regions of interest prior to exposure to the test substance and after exposure to the test substance. It is apparent that, in the practice of the invention, the response curves generated depict high-quality representations of individualized and/or aggregate cellular behavior. Thus, comparison of the response curves of the regions of interest before and after exposure to the test substance depict the direct effect of a test substance on the plurality of cells and permit accurate predictions to be made of the effect of a substance on an integrated cellular system from which the plurality of cells was derived. Changes in electrical excitability may, for example, be assessed based on the presence or absence of a response-time curve (elicited by a stimulation protocol of regularly-applied stimuli with either progressively increasing or decreasing amplitude) used to define a threshold for the contractile response. Specific applications of the present invention include, for example, prediction of the adverse effects of drug substances on heart tissue.

In preferred embodiments of the invention, the cells are cardiac myocytes (of either ventricular or atrial origin), which are placed and imaged in an experimental chamber, preferably a flowcell, and maintained at a predetermined temperature. Preferably, for optimum studies of behavior of the plurality of cells, the temperature is at or near physiologic temperature, although other temperatures may be used. The non-contiguous cardiac myocytes may be obtained by known methodologies such as heart muscle disaggregation. Preferably, the plurality of cells subjected to a stimulation protocol are stimulated using a field stimulation of 1.0 Hertz during superfusion with HEPES-buffered Tyrode's solution. Test substances are preferably superfused with the test substance contained in a physiologic salt-buffer solution. Each plurality of cells is preferably visualized at magnifications of 1-3×. Video is recorded at a preferred sampling of 30 Hz or greater.

In preferred embodiments, the invention includes analysis of video recordings of multiple experimental chambers, each containing a plurality of cells to be analyzed. In such embodiments, one or more experimental chambers may be viewed with a single video imaging device, where the imaging device and the chamber(s) can be moved relative to each other. Alternately, multiple video imaging devices may be dedicated to one or more experimental chambers and their physical positions fixed relative to each other. Video capture and analysis for each chamber may proceed in parallel according to the techniques described above. Such embodiments provide for parallel assays at any given time and permit simultaneous examination of the effects of multiple test substances, varying concentrations of test substances, or both. For each chamber it is also possible to evaluate concentration-response relationships to test substances by controlling the concentration of test-substance in each chamber and repeating the experimental protocols.

In preferred embodiments, multiple video recordings of the plurality of cells after exposure to the test substance may be made to coincide with exposure of the plurality of cells with differing concentrations of the test substance, or a differing test substance. Such recordings would be analyzed in accordance with the inventive method as described above.

In preferred embodiments, the invention utilizes off-line or on-line analysis software, either online or within an internal network, permitting automated selection of cellular regions and/or regions of interest, based upon predefined contractile parameters, automated addition of test substance, data collection and compilation and report generation. Furthermore, response-time curves and any values calculated therefrom may be stored for later reference, so that the invention need not be implemented subsequent times on the same plurality of cells. Thus, the invention provides for a system to simultaneously evaluate the effects of test substances on multiple pluralities of cells.

In particularly preferred embodiments, the invention describes an automated in vitro QT screening assay to evaluate both accelerated and delayed repolarization based on changes in twitch contractions and refractoriness of isolated cardiac ventricular myocytes or cardiac stem cells. In the practice of the assay, which includes the video recording and data analysis methodologies described above, the effect of drugs that impact cardiac repolarization, inotropic status, and excitability, and are linked to proarrhythmia is readily and rapidly evaluated. Concentration-dependent effects can be evaluated as part of the characterization of the drug and represented as concentration-response curves. Positive and negative inotropic effects on cardiac contractility are evaluated based on the amplitude of the contractile responses. The assay permits a rapid and facile assessment of cellular, particularly myocyte, expansions and/or contractions using optically based pixel change techniques, programmable electrical stimulation, and computer analysis, negating the need for time-limiting (and labor-intensive) microelectrode recordings and analysis. Further, the assay may quickly and efficiently meet an urgent need for a functional, integrated repolarization assay with higher throughput to screen compounds for cardiac QT repolarization liabilities. The assay provides several advantages over current methods, which are not suited for high throughput screening due to both limitations in throughput by required experimental conditions (including long recovery and equilibration periods, and a small number of fibers per muscle tissue), manpower costs, and animal usage. Furthermore, as a result of using optical methods to measure cellular responses and evaluating cells that are not members of an integrated cellular system (i.e., non-contiguous cells) under controlled physiologic conditions, the methods described herein are easier to perform and less time-consuming than prior methods, and obviate the need for microelectrode recording techniques to evaluate electrophysiologic responses to chemicals and drugs.

Figure 2:
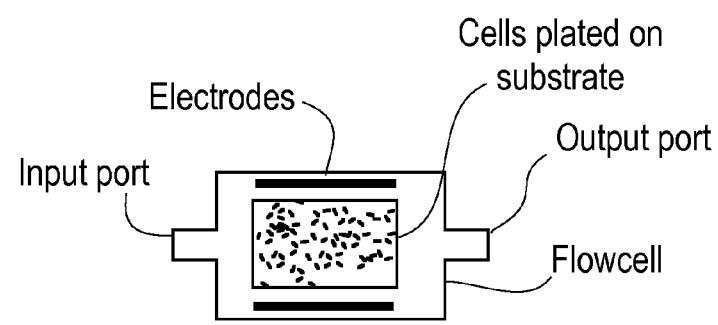
FIG. 2 illustrates an example of an apparatus for the practice of the method of the invention.
Figure 2:
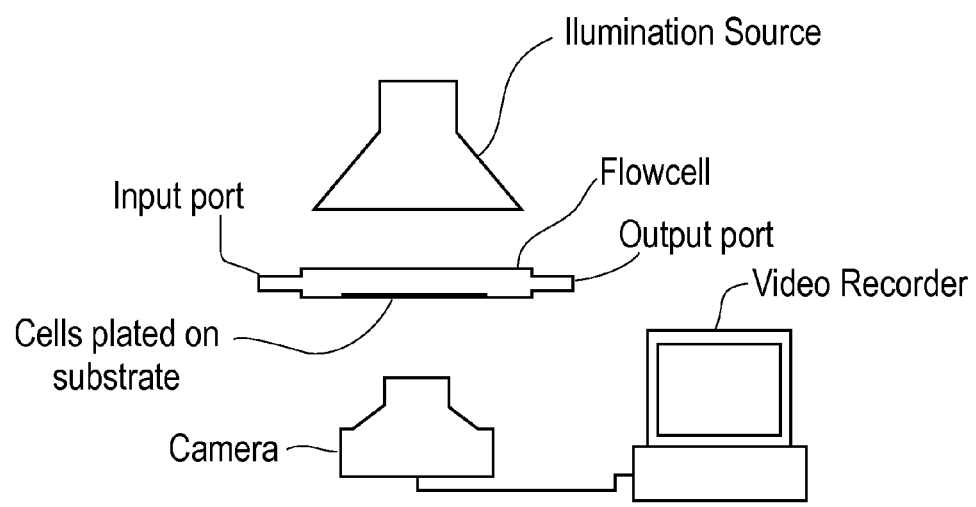
Figure 3:
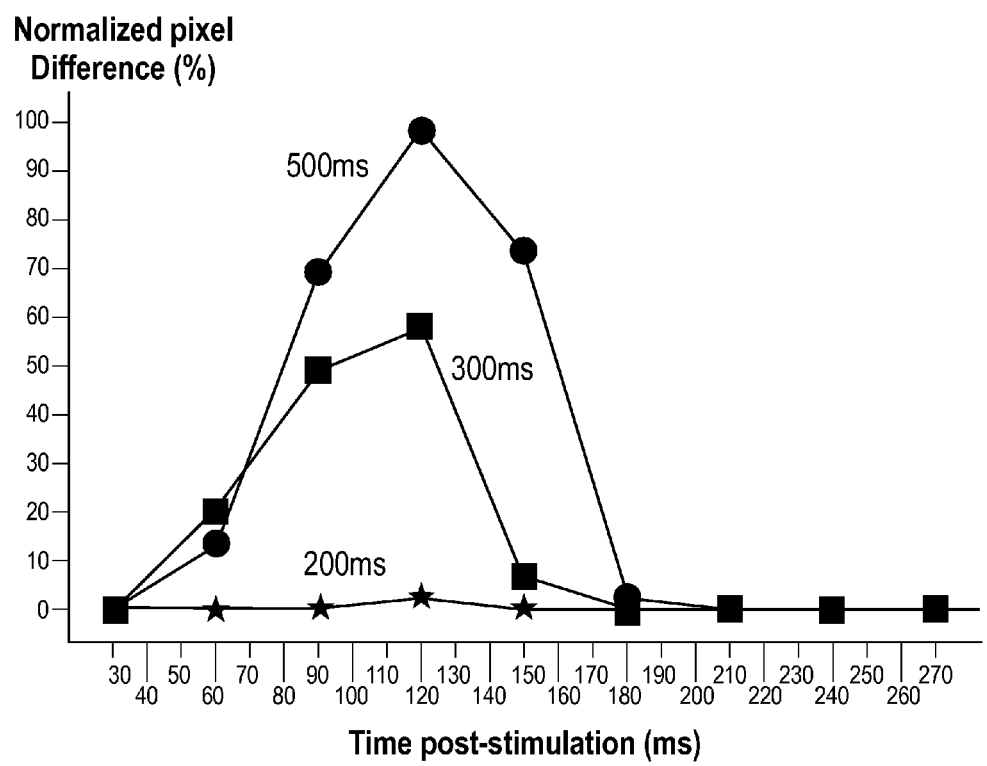
FIG. 3 illustrates the superimposed response-time pixel counts (normalized to the average pacing response) for a pacing protocol with premature stimuli on a group of myocytes.

Thus, the assay in accordance with the invention can evaluate changes in refractoriness in isolated myocytes on the basis of contractile responses to electrical stimulus. The results illustrated in the FIGS. 1-4 demonstrate the basic technique and recordings obtained when evaluating the effective refractory period of a group of isolated cardiac myocytes in accordance with the invention. FIG. 2 illustrates an example of a physical apparatus used for stimulating and recording. FIG. 1 illustrates a typical stimulation protocol and stylized responses. In FIG. 1, ventricular myocytes were stimulated electrically using a paired pulse protocol in which myocytes were paced (using field stimulation) using a stimulus train of 3 pulse groups each comprised of 3 pacing stimuli at 1 s intervals and a premature stimulus whose interval was variable. The effective refractory period (ERP) was defined as the longest premature stimulus interval that fails to trigger a measurable myocyte contractions equal in magnitude to 25% of the average regular paced response. FIG. 3 illustrates the superimposed pixel count responses (normalized to the average pacing response) for premature stimuli at intervals of 500, 300, and 200 milliseconds. The ERP measured for this group of myocytes was between 200-300 milliseconds and may be linearly interpolated to be 240 ms. Greater resolution may be achieved by decreasing the step size of the incremental premature pulses.

In this example, field stimulation was achieved by two platinum electrodes connected to a biphasic square wave stimulator. The duration of a single stimulus pulse was 5 milliseconds, while intensity was set at one hundred twenty percent (120%) above threshold which is approximately 7 volts/cm. Bath temperature was maintained at a controlled temperature at or near physiologic temperature. Pacing signals and myocyte contractions were simultaneously recorded.

In an embodiment of the invention an apparatus is provided to present living cells for digital imaging during measurement for response of the cells to a test substance. In this embodiment, the apparatus serves to store and nourish the living cells until the time they are tested, to transport the living cells from one section of the apparatus to another, and to present the living cells to the digital recording apparatus while exposing the cells to a test substance, for example a drug, and optionally to an electrical stimulation protocol. An apparatus in accordance with the invention includes a fluid channel having a fluid inlet port at an inlet end and a fluid exit at an outlet end; a fluid pumping device connected to the inlet port of the fluid channel; a strip of optically transparent or semi-transparent film running through the fluid channel; the film capable of adhering to living cells; at least one flowcell positioned over the film, the flowcell comprising a cavity having an optically transparent upper surface and side walls capable of forming a seal with the film to form an enclosed environment; and a vertical actuator connected to the at least one flowcell capable of elevating the at least one flowcell above the film or lowering the at least one flowcell on to the film.

In a preferred embodiment the apparatus to store and nourish the living cells comprises an elongated fluid channel 501 having a fluid inlet port 502 at an inlet end 503 and a fluid exit or drain port 504 at an outlet end 505. In one preferred embodiment the fluid channel 501 dimensions are approximately 1" wide×⅞" deep×36" long. In this embodiment a suitable fluid pumping device, for example a peristaltic pump, is connected to the inlet port 502 of the fluid channel 501 so that certain fluids, for example buffer solutions 506, can be maintained at a desired level 507 and flowed from the inlet end 503 of the fluid channel 501 to the outlet end 505 in order to nourish the living cells 601. Also, in a preferred embodiment a device 508 to heat a section of the fluid channel 501 to a temperature at or near physiological temperatures is provided so that living cells 601 in this region of the fluid channel 501 can be maintained at or near physiological temperatures.

In a preferred embodiment of the invention the apparatus to transport the living cells 601 is achieved by plating the living cells 601 onto a strip of optically transparent or semi-transparent, flexible, polymer film 602. In one preferred embodiment the polymer film 602 measures approximately 0.005" thick×⅞" wide×46" long. In another preferred embodiment the polymer film 602 comprises a continuous strip of FEP (fluorinated ethylene propylene) film which has been specially treated, for example by plasma polymerization of an amine functionalized sub layer 603, to promote attachment of the living cells 601 to the polymer film 602. In accordance with this embodiment the continuous strip of cell-plated polymer film 601,602 is translated as needed by a pinched-roller motorized drive mechanism 509.

In a preferred embodiment the living cells 601 are presented to the digital recording apparatus 801 and exposed to a test substance by positioning a section of the cell-plated polymer film 601,602 under a cluster of one or more flowcells 701 wherein each flowcell 702 comprises a cavity 803 having an optically transparent upper surface 804 and elastomeric side walls 805 to facilitate sealing to the polymer film 602. In one preferred embodiment the dimensions of each flowcell are approximately 1.5 mm wide×1.5 mm tall×8 mm long. In this embodiment openings 703 are provided at each end of the flowcells so that a test substance may be injected at one end and exited from the other end. Optionally in this embodiment the openings 703 at each end of the flowcell include electrical contacts which are used to administer an electrical stimulation protocol to the living cells. Also in this embodiment the cluster of one or more flowcells 701 is connected to clamping mechanism 806 comprised of a motorized vertical actuator 807 and connection bracket 808 so that the flowcells may be elevated above or forcibly clamped against the top surface of polymer film 602. When clamped each flowcell forms an independent, reversible, and completely enclosed environment 809 around a selection of living cells allowing for introduction of a test substance, administration of an optional electrical stimulation protocol, and digital video recordings of the enclosed living cells 601.

Although particular embodiments of the invention have been described in detail herein with reference to the accompanying drawings, the invention is not limited to those particular embodiments, and various changes and modifications may be affected therein by one skilled in the art without departing from the scope or spirit of the invention, as claimed.

What is claimed is:

1. An apparatus for presenting living cells for digital imaging during measurement for response of the cells to a test substance, the apparatus comprising:
   a fluid channel having a fluid inlet port at an inlet end and a fluid exit at an outlet end;
   a fluid pumping device connected to the inlet port of the fluid channel;
   a strip of optically transparent or semi-transparent film configured to translate through the fluid channel; the film capable of adhering to living cells;
   at least one flowcell positioned over the film, the flowcell comprising a cavity having an optically transparent upper surface and side walls capable of forming a seal with the film to form an enclosed environment; and
   a vertical actuator connected to the at least one flowcell capable of elevating the at least one flowcell above the film or lowering the at least one flowcell on to the film.

2. The apparatus of claim 1, further comprising a heating device to heat a portion of the fluid channel.

3. The apparatus of claim 1, wherein the strip of optically transparent or semi-transparent film is continuous.

4. The apparatus of claim 1, wherein the at least one flowcell further comprises electrical contacts at each end capable of administering an electrical stimulation protocol to the living cells.

* * * * *